(12) United States Patent
Wang et al.

(10) Patent No.: US 9,943,272 B2
(45) Date of Patent: Apr. 17, 2018

(54) X-RAY LASER MICROSCOPY SYSTEM AND METHOD

(71) Applicant: Rising Star Pathway, a California Corporation, Cupertino, CA (US)

(72) Inventors: Yiming Wang, Richmond, TX (US); Vincent Huang, Cupertino, CA (US); Hanjie Zou, Chengdu (CN); Eileen Guo, Palo Alto, CA (US); Ruibo Wu, Saratoga Springs, UT (US); Zhuotong Xian, San Jose, CA (US)

( * ) Notice: Subject to any disclaimer, the term of this patent is extended or adjusted under 35 U.S.C. 154(b) by 0 days.

(21) Appl. No.: 15/713,645

(22) Filed: Sep. 23, 2017

(65) Prior Publication Data

US 2018/0020996 A1    Jan. 25, 2018

Related U.S. Application Data

(63) Continuation-in-part of application No. 15/442,670, filed on Feb. 26, 2017, which is a continuation-in-part
(Continued)

(51) Int. Cl.
*A61B 6/00* (2006.01)
*G21K 7/00* (2006.01)
(Continued)

(52) U.S. Cl.
CPC ..... *A61B 6/4064* (2013.01); *G01N 23/20008* (2013.01); *G21K 7/00* (2013.01); *G01N 23/083* (2013.01); *G01N 23/223* (2013.01)

(58) Field of Classification Search
CPC ....................................................... G21K 7/00
See application file for complete search history.

(56) References Cited

U.S. PATENT DOCUMENTS 5,177,774 A * 1/1993 Suckewer ............... G21K 7/00
378/43
5,245,648 A * 9/1993 Kinney ............... G01N 23/046
378/145
(Continued)

OTHER PUBLICATIONS

Dennison et al. (1992), Ultrahigh Vacuum chamber for synchrotron x-ray diffraction from films absorbed on single crystal surfaces; Rev. Sci. Instrum. 63(8). pp. 3835-3841.*
(Continued)

*Primary Examiner* — David J Makiya
*Assistant Examiner* — Soorena Kefayati
(74) *Attorney, Agent, or Firm* — Stephen E. Zweig

(57) ABSTRACT

Improved system and method of X-ray laser microscopy that combines information obtained from both X-ray diffraction and X-ray imaging methods. The sample is placed in an ultra-cold, ultra-low pressure vacuum chamber, and exposed to brief bursts of coherent X-ray illumination further concentrated using X-ray mirrors and pinhole collimation methods. Higher resolution data from a sample is obtained using hard X-ray lasers, such as free electron X-ray lasers, and X-ray diffraction methods. Lower resolution data from the same sample can be obtained using any of hard or soft X-ray laser sources, and X-ray imaging methods employing nanoscale etched zone plate technology. In some embodiments both diffraction and imaging data can be obtained simultaneously. Data from both sources are combined to create a more complete representation of the sample. Methods to further improve performance, such as concave or curved detectors, improved temperature control, and alternative X-ray optics are also disclosed.

19 Claims, 8 Drawing Sheets

Related U.S. Application Data of application No. 15/218,017, filed on Jul. 23, 2016, now Pat. No. 9,583,229.

(51) Int. Cl.
  *G01N 23/20* (2018.01)
  *G01N 23/083* (2018.01)
  *G01N 23/223* (2006.01)

(56) References Cited

U.S. PATENT DOCUMENTS

| | | | | |
|---|---|---|---|---|
| 5,319,693 | A * | 6/1994 | Eberhard | A61B 6/032 378/19 |
| 5,450,463 | A * | 9/1995 | Iketaki | G21K 7/00 378/43 |
| 5,864,599 | A * | 1/1999 | Cowan | G21K 7/00 378/43 |
| 6,529,578 | B1 * | 3/2003 | Taguchi | G21K 1/06 378/119 |
| 6,823,039 | B2 * | 11/2004 | Hoheisel | A61B 6/032 378/19 |
| 6,859,313 | B2 * | 2/2005 | Iketaki | G02B 21/06 250/458.1 |
| 7,183,547 | B2 * | 2/2007 | Yun | B82Y 10/00 250/310 |
| 7,235,790 | B2 * | 6/2007 | Hoge | G01T 1/1648 250/370.09 |
| 7,466,796 | B2 * | 12/2008 | Bloom | G21K 7/00 378/43 |
| 7,822,174 | B2 * | 10/2010 | Le Gros | G21K 7/00 378/43 |
| 8,450,683 | B2 * | 5/2013 | Yamazaki | H01J 37/28 250/306 |
| 8,602,648 | B1 * | 12/2013 | Jacobsen | G21K 7/00 378/208 |
| 9,074,992 | B2 * | 7/2015 | Ozawa | G01N 23/207 |
| 9,594,036 | B2 * | 3/2017 | Yun | G01N 23/223 |
| 9,823,203 | B2 * | 11/2017 | Yun | H01J 35/08 |
| 2014/0087321 | A1 * | 3/2014 | Waniuk | F27B 14/061 432/13 |
| 2015/0369759 | A1 * | 12/2015 | Mazor | G01N 23/201 378/89 |
| 2017/0261442 | A1 * | 9/2017 | Yun | G01N 23/04 |

OTHER PUBLICATIONS

K.J. Gaffney, et. al., "Imaging Atomic Structure and Dynamics with Ultrafast X-ray Scattering", Science 316, 1444 (2007). Entire document.

Chang and Sadkinawat, "Ultra-high aspect ratio high-resolution nanofabrication for hard X-ray diffractive optics", Nature Communications 5:4243 (2014). Entire document.

Chao et. al., "Soft X-ray microscopy at a spatial resolution better than 15nm", Nature 435, Jun. 30, 2005, pp. 1210-1213. Entire document.

Kang, et. al., "Nanometer Linear Focusing of Hard X Rays by a Multilayer Laue Lens", Physical Review Letters 96, Mar. 31, 2006, pp. 127401-1 to 127401-4. Entire document.

* cited by examiner

Figure 2A
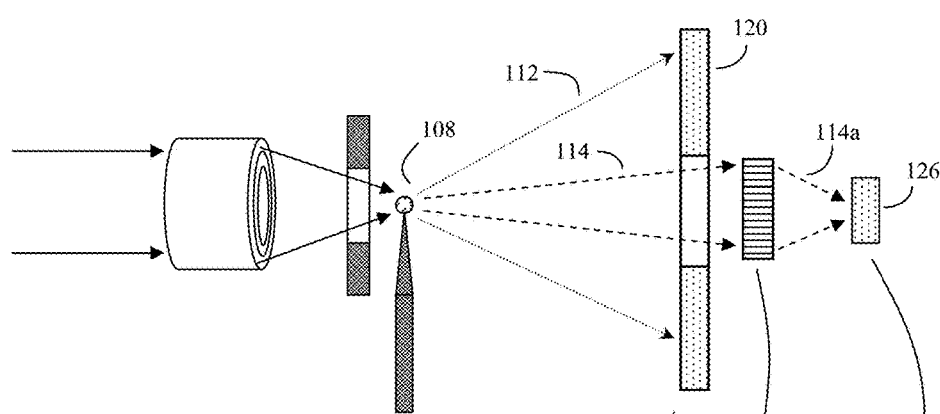
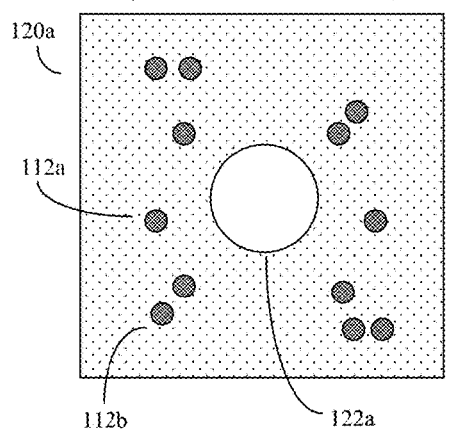
Figure 2B
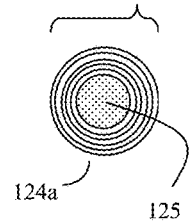
Figure 2C
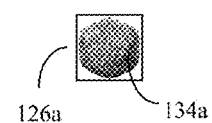
Figure 2D

X-RAY LASER MICROSCOPY SYSTEM AND METHOD

CROSS REFERENCE TO RELATED APPLICATIONS

This application is a continuation in part of U.S. patent application Ser. No. 15/442,670, "X-RAY LASER MICROSCOPY SAMPLE ANALYSIS SYSTEM AND METHOD", filed Feb. 26, 2017; application Ser. No. 15/442,670 is a continuation in part of U.S. patent application Ser. No. 15/218,017 "IMPROVED X-RAY LASER MICROSCOPY SYSTEM AND METHOD", filed Jul. 23, 2016, now U.S. Pat. No. 9,583,229, issued Feb. 28, 2017; the entire contents of these applications are incorporated herein by reference.

BACKGROUND OF THE INVENTION

Field of the Invention

This invention is in the field of X-ray laser microscopy.

Description of the Related Art

The resolving power of conventional optical microscopes is limited by the wavelength of light. Thus over the years, various methods employing shorter wavelength particles, such as electrons, and shorter wavelength photons, such as X-rays, have been employed to achieve still higher levels of resolution.

X-ray radiation spans a range of wavelengths in the nanometer region, generally ranging from about 10 nanometers (soft X-rays) with energies of around 100 electron volts, to about 0.01 nanometers (hard X-rays) with energies up to about 10,000 electron volts. Photons with energies above this are typically referred to as gamma rays. Since many molecular biological structures of interest have structural details in roughly the 10 to 0.1 nanometer range, scientists have turned to X-rays to help elucidate the structure of proteins, DNA, membranes, viruses, cells, and other biological structures of interest.

Due to the desirable aspects of coherent light sources, X-ray lasers are particularly useful for X-ray microscopy. Here various methods have been employed, including X-ray diffraction methods, X-ray holographic methods, and various types of X-ray imaging methods. Although X-ray mirrors and lenses are much more difficult to fabricate than their optical counterparts, various methods of focusing X-rays, including Wolter, Kirkpatrick-Baez, and Schwarzschild x-ray mirror designs, as well as various types of zone plate methods (which operate according to diffraction methods) have been devised.

Some recent improvements in zone plate technology includes the work of Chang and Sakdinawat, "Ultra-high aspect ratio high-resolution nanofabrication for hard X-ray diffractive optics" NATURE COMMUNICATIONS, 5:4243, Jun. 27, 2014, pages 1-7 (DOI: 10.1038/ncomms5243). They taught that improved zone plates can be produced using some of the same photolithographic methods used to produce modern integrated circuits and other nanostructures. These methods are also described by their US patent application 2015/037679.

Previous work in the X-ray microscopy field includes the soft X-ray imaging methods of Suckwer et. al., U.S. Pat. No. 5,177,774; Chao et. al, "Soft X-ray microscopy at a spatial resolution better than 15 nm", NATURE, Vol 435, Jun. 30, 2005, pages 1210 to 1213; and Kirtz et. al., "Soft X-ray microscopes and their biological applications", Q. Rev. Biophys. 28, 33-130 (1995).

Other workers have used ultra-short bursts of hard X-rays, often produced by free electron lasers, and X-ray diffraction methods, to elucidate structures at still higher resolution. This work includes Gaffney et. al., "Imaging Atomic Structure and Dynamics with Ultrafast X-ray Scattering", Science 316, Jun. 8, 2007, pages 1444-1448.

Despite these advances, the field remains challenging. The highest resolution laser microscopy sample details can generally only be obtained by using ultra-short hard X-rays, which are difficult to focus, and which tend to rapidly destroy the sample. Here, use of X-rays produced by free electron lasers, ultra-short bursts of energy, and X-ray diffraction methods (which do not require the sample scattered X-rays to be imaged) are favored.

By contrast, lower resolution laser microscopy, using soft X-rays, is a bit closer to conventional microscopy. Coherent soft X-ray light can be produced by a variety of different methods, and the lower energies tend to be less destructive of the sample. The soft X-rays, after being scattered by the sample, can be focused by various methods, such as various phase zone plate methods, resulting in a more conventional type magnified image of the sample.

Another problem is that the performance of existing X-ray laser microscopes can be limited by other effects, such as X-ray scattering or attenuation off of residual air molecules in the vacuum chamber, and by thermal effects (e.g. heating of the sample and X-ray lenses).

Commonly owned and invented parent U.S. Pat. No. 9,583,229 (application Ser. No. 15/218,017), "IMPROVED X-RAY LASER MICROSCOPY SYSTEM AND METHOD" described an improved X-ray microscopy system. Commonly owned and invented parent application Ser. No. 15/442,670, a continuation in part of patent application Ser. No. 15/218,017, taught improved methods of sample handling for such an X-ray microscopy system.

BRIEF SUMMARY OF THE INVENTION

As per commonly owned and invented U.S. Pat. No. 9,583,229 (application Ser. No. 15/218,017), and parent application Ser. No. 15/442,670, the present invention is also based, in part, on the insight that the lower resolution sample structural information produced by prior art hard X-ray laser systems, which rely on X-ray laser diffraction methods, is frequently lost. This is because larger (e.g. lower resolution) sample structural details do not end up substantially diffracting the angle of the X-ray laser beam. Instead, larger sized structural details only cause the X-rays to be diffracted at low angles from the main X-ray beam. Thus these larger sample structural details are not well separated from X-rays that pass completely through the sample (116) to any significant extent. This often shows up as the central "sun" in a "sunburst" type X-ray diffraction pattern. As an example, see Gaffney and Chapman, Science 316, 1444 (2007), FIGS. 3A and 3B, which illustrate how the center region of an X-ray diffraction pattern is essentially unreadable.

This invention is also based, in part, on the insight that this missing low resolution structural information could be provided by use of alternative X-ray imaging methods, such as phase zone plate methods, and that if the phase zone plate was positioned in an X-ray diffraction apparatus so that the phase zone plate only obscured a small portion of the center of the X-ray diffraction detector, little X-ray diffraction information would be lost because, as discussed above, the central portion of an X-ray diffraction detector has little value due to interference from the main X-ray beam that has passed completely through the sample.

The invention is also based, in part, on the insight that in this regard, advances in high-resolution nanofabrication methods have allowed for the fabrication of ultra-small zone plates capable of focusing even hard X-rays, as well as soft X-rays. Collimator devices with ultra-small (nanometer scale) collimator openings may also be produced using these methods.

The invention is also based, in part, on the insight that for higher performance, every effort must be made to reduce the damaging effects of X-ray beams on both the sample and on the various X-ray microscope components. In this regards, greater efforts to chill the devices to ultra-cold temperatures, by use of cryogenic fluids, possibly including even liquid helium, would be desirable. Further, to improve contrast, every effort must also be made to reduce the vacuum of the microscopy chamber to unusually low pressure levels.

Thus in some embodiments, the invention may be an improved X-ray laser microscopy method, equipped to analyze a given sample using (sometimes simultaneously) both X-ray diffraction and X-ray imaging methods onto different X-ray detector regions. Typically the higher resolution sample data will be obtained from the X-ray diffraction portion of the device, while the lower resolution sample data will be obtained from the X-ray imaging portion of the device. Both the X-ray diffraction data and the X-ray imaging data can be fed to a computer, which can be configured to use both sets of information to produce a combined view of the sample that provides more structural information than either one method could produce by itself.

To obtain X-ray imaging data with minimum loss of X-ray diffraction data, and with as short a wavelength of X-ray radiation as possible, the system may often make use of nanoscale etched zone plate technology.

The efficiency of the improved X-ray microscope can further be enhanced by chilling various portions of the device to ultra-low temperatures, and maintaining ultra-low vacuum during operation.

This method will typically use at least one X-ray laser providing coherent X-rays through an X-ray port (or other opening) into a vacuum chamber. Inside the vacuum chamber, a first X-ray optical device, such as an X-ray mirror device, will focus or collimate the coherent X-rays onto the sample.

The present application builds on the teaching of commonly owned and invented parent U.S. Pat. No. 9,583,229 (application Ser. No. 15/218,017) and parent application Ser. No. 15/442,670. Here, additional methods to further improve performance, such as curved detectors, improved temperature control, and alternative X-ray optics are also disclosed.

BRIEF DESCRIPTION OF THE DRAWINGS

FIG. 2A shows a detail of some of the various X-ray laser microscopy components previously shown in FIG. 1.

FIG. 2B, shows a drawing of the first outer portion of the X-ray detection apparatus as seen from an orthogonal angle.

FIG. 2C shows a drawing of the second X-ray optical device (e.g. phase zone plate) as seen from an orthogonal angle.

FIG. 2D shows a drawing of the second inner portion of the X-ray detection apparatus as seen from an orthogonal angle.

DETAILED DESCRIPTION OF THE INVENTION

Figure 1:
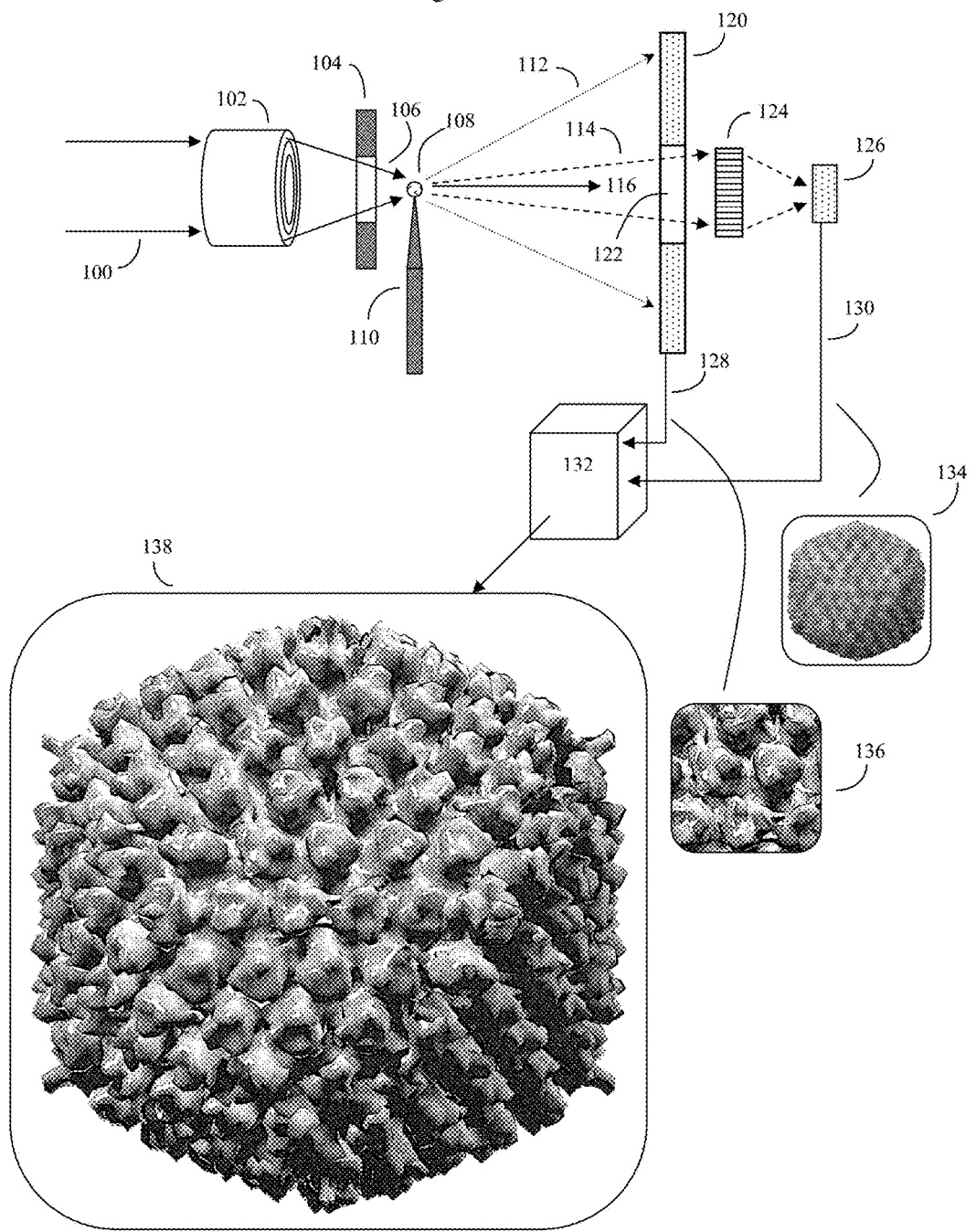
FIG. 1 shows an overview of the improved X-ray laser microscopy method.
Figure 4:
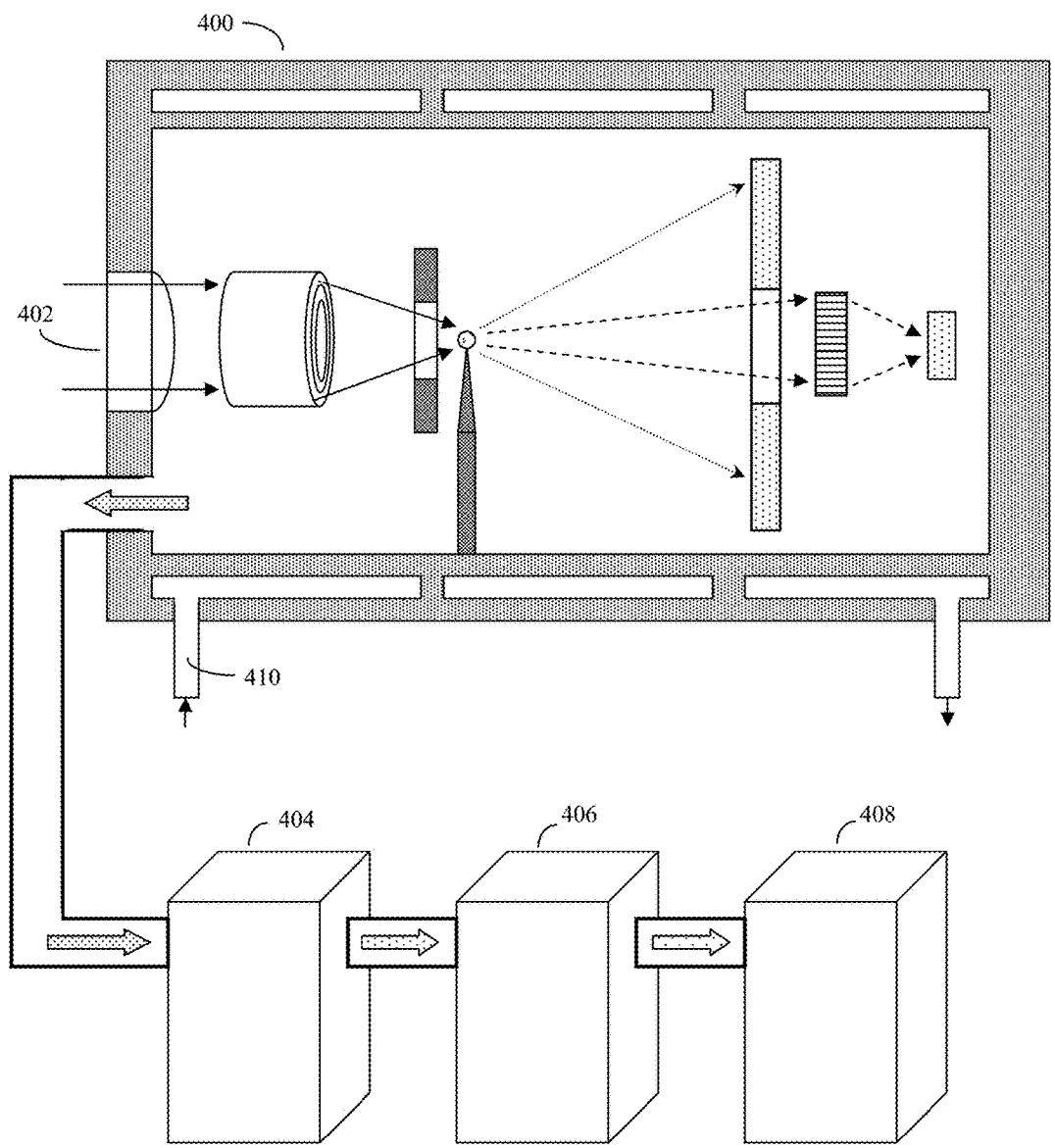
FIG. 4 shows some additional components, such as a vacuum chamber, that are also used in the improved X-ray laser microscopy method.

Here it will be useful to refer to both FIG. 1 and FIG. 4.

FIG. 1 shows an overview of the improved X-ray laser microscopy method, while FIG. 4 gives more details about the microscope's vacuum chamber, vacuum pump system, and X-ray port arrangement.

In some embodiments, the invention may be a system, device or method of X-ray laser microscopy, typically using at least one X-ray laser (not shown), which will supply a coherent source of X-ray illumination (100), typically through an X-ray port (402) into a vacuum chamber (400) configured to hold many of the other X-ray microscope components. In the following description, unless otherwise specified or drawn, assume that the various methods and components that are described are inside of a vacuum chamber (400).

Note that typically the X-ray port will be composed of a substantially vacuum tight but X-ray resistant material. However in the case where the X-ray laser itself is under the same vacuum conditions as the vacuum chamber, then the X-ray port may be a simple opening in the side of the vacuum chamber.

This coherent source of X-ray illumination can be provided by various types of X-ray lasers, and indeed in some embodiments, it may be useful to use more than one type of X-ray laser (e.g. a hard X-ray laser and a soft X-ray laser). These X-ray lasers can be any of a free-electron laser, capillary plasma-discharge laser, solid-slab target laser, optical field excited plasma laser, high-harmonic generation laser, and the like.

Since the beam size of coherent X-ray light sources (100) is usually significantly larger than the size of the microscopy sample (108), it will typically be useful to use a first X-ray optical device (102) configured to focus and/or collimate the X-rays onto the microscopy sample (sample) (108). A sample administrator (110) will control the position of the sample.

X-rays (106) focused by the first X-ray optical device (102) typically impinge on the sample (108), where some X-rays (112, 114) are scattered or diffracted at various angles by the sample, while other X-rays pass (116) completely through the sample on their original paths without any significant deflection. At least some of these X-rays (e.g. at least 112) are in turn detected by a detection apparatus (120). Typically, the configuration of the X-ray microscope inside the vacuum chamber is such that the first X-ray optical device (102) is disposed in between the X-ray port (402) and the sample (108) (e.g. sample position controlled by the sample administrator 110), and the sample (again as controlled by the sample administrator 110) is substantially in between the first X-ray optical device (102) and the detection apparatus (120).

This first X-ray optical device (102), as well as optionally the second X-ray optical device (124) will typically comprise at least one X-ray mirror formed from a plurality of curved X-ray reflecting surfaces. Here, X-ray mirror designs such as various Wolter, Kirkpatrick-Baez, or Schwarzschild x-ray mirror designs may be used.

In some embodiments, at least the exposed mirror surfaces of these X-ray mirror designs may comprise X-ray resistant, X-ray reflecting materials, such as silicon, boron, silicon triboride, and the like.

As will be discussed shortly, the detection apparatus may contain more than one portion (e.g. detection region). Usually the detection region will comprise at least a first outer region (120) configured to detect both the location and intensity of various X-rays (112) that have been diffracted away from the main X-ray beam (116).

Use of three stage vacuum pumps: In operation, to reduce interference from air molecules, which can both absorb and scatter the coherent X-rays, thus reducing microscopy performance, the pressure inside the vacuum chamber (400) will typically be reduced to very low pressures, often on the order of $10^{-9}$ Torr or less, usually by using at least one exterior vacuum pump system (e.g. 404, 406, 408). This system may be a multiple stage vacuum pump. For example, a three stage vacuum pump system, where the first stage may be a positive displacement pump, the second stage may be a sorption pump, and the third stage may be any of a cryopump, turbo molecular pump, and/or an ion pump may be used.

The sample administrator (110) will be used to control the position of the microscopy sample(s) (108). In some embodiments, such as when the sample administrator (110) holds the sample (108) on the end of a pin like structure, the sample may be introduced to the vacuum chamber (400) before the pressure is reduced. In other configurations, such as when the sample administrator is used to inject or place the sample into the vacuum chamber at a defined location, the sample may be introduced into the vacuum chamber after the vacuum has been reduced.

Various methods may be used to inject or place the sample. The sample may be placed into position at the end of a simple pin-like holder, or more complex robotic sample handing device. Alternatively the sample may be injected as a stream of small moving particles, as per the methods of Gaffney, Science 316, 1444 (2007).

The X-rays used in this microscopy method are very energetic, and can heat X-ray optical elements (e.g. mirror systems 102, zone plates 124, etc.) to high temperatures. This heating is undesirable, both from the standpoint of preserving the structure of the X-ray optical elements (102, 124), as well as in causing undesired frequency wavelength shifts in the X-rays interacting with the X-ray optical elements, thus reducing the resolution of the microscope. To reduce these effects, thus increasing both the lifetime and the performance of the various X-ray optical elements, it will often be useful to chill at least some of the various X-ray optical elements (102, 124) to low temperatures, preferably extremely low temperatures such as 20 degrees Kelvin or less.

In at least one mode of operation of the X-ray microscope, the system will use the X-ray port (402) to provide a very short burst of coherent X-rays (100), as well as use the first X-ray optical device (102) to focus and/or collimate this burst of coherent X-rays onto the microscopy sample (108) (position determined by the sample administrator 110). The system will then use at least the first portion of the detection apparatus (120, 120a) to detect a first signal from the sample. This first signal will be at least some of the spatially separated X-rays (112, 112a, 112b) that have been diffracted at various angles by the microscopy sample (108).

For at least hard X-ray lasers, very short bursts of illumination are preferable. This is because the X-ray burst will usually completely destroy the sample. However if the burst duration is kept extremely short, the various atomic components of the sample, although essentially exploding outward, will not have enough time to move significantly over the duration of the burst. Here extremely short bursts of coherent X-rays, often between about $10^{13}$ seconds (100 femtoseconds) and $10^{-17}$ seconds (10 attoseconds), or even shorter are often preferred. Because softer X-rays are much less destructive, however, longer duration bursts may be used when soft X-ray lasers are used.

At least the first signal (data from the detectors 128) may then be used to determine the structure of the sample by any means desired. However in a preferred embodiment, the system will use at least one computer processor (132) to collect at least first signal data (128) pertaining to the location and intensity of these X-rays (112a, 112b), and reconstruct a likely representation of a structure of the microscopy sample at approximately a nanometer level of resolution (136). Here, "nanometer level" is typically between about 10 to 0.1 nanometers of resolution, or more broadly between about 20 to 0.01 nanometers of resolution.

Thus returning to FIGS. 1 and 4, and to reiterate, coherent X-rays are obtained from an X-ray port (see FIG. 4 402) and are focused and collimated by a first X-ray optical device (X-ray mirror) (102) and often an optional pinhole collimator (104). This pulse of focused coherent X-rays (106) is then used to illuminate one or more microscopy samples (108) that have been positioned with a sample administrator (110). The pinhole collimator is generally composed of an X-ray opaque material with a smaller pinhole. The X-ray opaque material blocks off-angle X-rays, and the pinhole generally only allows the collimated or focused X-rays to reach the sample (108).

Put alternatively, the at least one X-ray mirror (102) may be configured to work in conjunction with a pinhole collimator (104) to concentrate collimated coherent X-rays (106) onto the microscopy sample (108) on or positioned by the sample administrator (110).

As previously discussed, the sample administrator (110) can be anything from a pin used to place the sample (108) in the correct position, or it may be a more complex device, such as a sample injection port configured to dispense a plurality of small droplets of particles of sample into the vacuum chamber at the correct position and correct times. When the sample administrator is an injection port, the microscope may be configured to obtain data from a plurality of similar type samples, (e.g. a plurality of virus particles), and to use this data from a plurality of samples to deduce an average structure of the plurality of samples.

As previously discussed, some of the coherent X-rays are diffracted (112) or scattered (114), and the X-rays diffracted at greater angles convey information regarding the smaller scale details of the sample. Other coherent X-rays (114) are diffracted or scattered at smaller angles, while many X-rays pass completely through the sample (116). Thus the smaller angle X-rays (114) tend to be more useful for obtaining lower resolution imaging data (e.g. will report on the larger structural aspects of the sample), and at the same time, tend to be less useful for diffraction structure reconstruction purposes because of interference from the main X-ray beam (116).

As previously discussed, in a preferred embodiment of the invention, a more complex set of X-ray optical elements and detectors may be used. In this preferred embodiment, the detection apparatus may comprise at least a first outer portion (120, 120*a*) and a second inner portion (126 or 126*a* or 126*b*). This preferred embodiment will also comprise at least one additional second X-ray optical device (124, or 124*a* or 124*b*) configured to focus X rays diffracted or scattered from the sample (108) at smaller angles. This second X-ray optical device (124, 124*a,* 124*b*) will also reside inside vacuum chamber (400). It (124) focuses X-rays obtained from microscopy sample (108) onto a second inner portion of said detection apparatus (126, or 126*a,* or 126*b*), thereby producing a second signal from the second X-ray optical device.

Due to the X-ray focusing characteristics of the second X-ray optical device, this second signal is typically a magnified (but lower resolution) image of the sample (108), as is shown in (134). In this preferred embodiment, the at least one computer processor (132) will typically be further configured to use both the first signal (128) from the first outer portion of the detection device (120) as well as a second signal (130) from a second inner portion of the optical detection device (126) to reconstruct a likely representation of a structure of said microscopy sample at a nanometer level of resolution.

The X-rays diffracted at greater angles (112) by sample (108) can be detected by a first outer portion of an X-ray detection apparatus (120) without need of further X-ray focusing systems. However to make better use the smaller angle scattered or diffracted X-rays (114), a second X-ray optical device may be used. Although this second X-ray optical device may also be an X-ray mirror device, in a preferred embodiment, one or more nanometer scale X-ray zone plates (124) that focus least some of the narrower angle X-rays (114) onto a second inner portion of an X-ray detection apparatus (124) are preferred. These nanometer scale X-ray zone plates may be fabricated according to the methods of Sakdinawat and Chang, US patent publication 2015/0376798, the entire contents of which are incorporated herein by reference.

Briefly, these fabrication methods work by forming a metal pattern on a substrate surface, such as a silicon surface by forming hole concentration balancing structures onto the substrate proximal to this pattern. Then directionality controlled features are etched from the substrate surface into the substrate by metal-assisted chemical etching. The concentration of balancing structures is used to control the direction of these features. Alternative fabrication methods may also be used.

Put alternatively, in the example configuration shown in FIG. 1, the detection apparatus comprises a first outer portion (120) comprising a larger multi-pixel solid state X-ray detector configured to capture and detect most of the greater angle diffracted X-rays. Here this X-ray detector (120) (and often 126 as well) may comprise a plurality of spatially separated, solid state, detector elements.

In a preferred embodiment, this first outer portion of the detector (120) further comprises a central hole (122) or other type opening through which the narrower angle X-rays (114) and main X-ray beam (116) can pass. In this embodiment, on or near the central hole (122) (such as on the other side of the hole) is a second X-ray optical device, such as a nanometer scale zone plate device (124), as well as a second inner portion of the detection apparatus, (126). This second inner portion (126) can either also be a multi-pixel solid state X-ray detector as well (possibly with different characteristics), or alternatively can be a different type of X-ray detector device.

To illustrate the concepts in more detail, remember that as previously discussed, data (128) from both the first portion of the detection apparatus (120) and data (130) from the second portion of the apparatus (124) are sent to one or more computer processor(s) (132), which can use this data to reconstruct a representation of the structure of the microscopy sample.

In FIG. 1, as an example, assume that the microscopy sample (108) is that of an adenovirus, such as a type 5 adenovirus that, at a lower level of resolution (134), can be seen to have an overall icosahedral structure. At a higher level of resolution (136), as we go towards the nanometer level of resolution, we see that the adenovirus has an outer coat composed of hundreds of adenovirus capsomers, which in turn are composed of multimeric protomer proteins, each with a characteristic structure of amino acids arranged in polypeptide chains.

From an X-ray laser microscopy perspective, the higher resolution (e.g. nanometer level) aspects of the adenovirus structure (128, 136) will convey information pertaining to the internal structure of the various protomers, how these protomers in turn assemble into the capsomers, and the relative spacing of the capsomers. By contrast, the lower resolution aspects of the adenovirus structure will tend to convey information as to the overall icosahedral shape of the virus, and how the various capsomers assemble on a larger scale (130, 134). By using both types of information (130, 134) and (128, 136), the computer processor can produce a more accurate representation of the adenovirus sample (138) that incorporates both the detailed nanometer scale information pertaining to capsomer structure, as well as showing the overall icosahedral structure of the adenovirus as well.

FIG. 2A shows a detail of some of the various X-ray laser microscopy components previously shown in FIG. 1.

FIG. 2B, shows a drawing of the first outer portion of the X-ray detection apparatus (120) as seen from an orthogonal angle (120a). Here various rays of X-ray light (112a, 112b) diffracted from the sample (108) hit the detection apparatus different locations and intensities, creating different patterns of diffraction spots (112a, 112b).

Figure 2E:
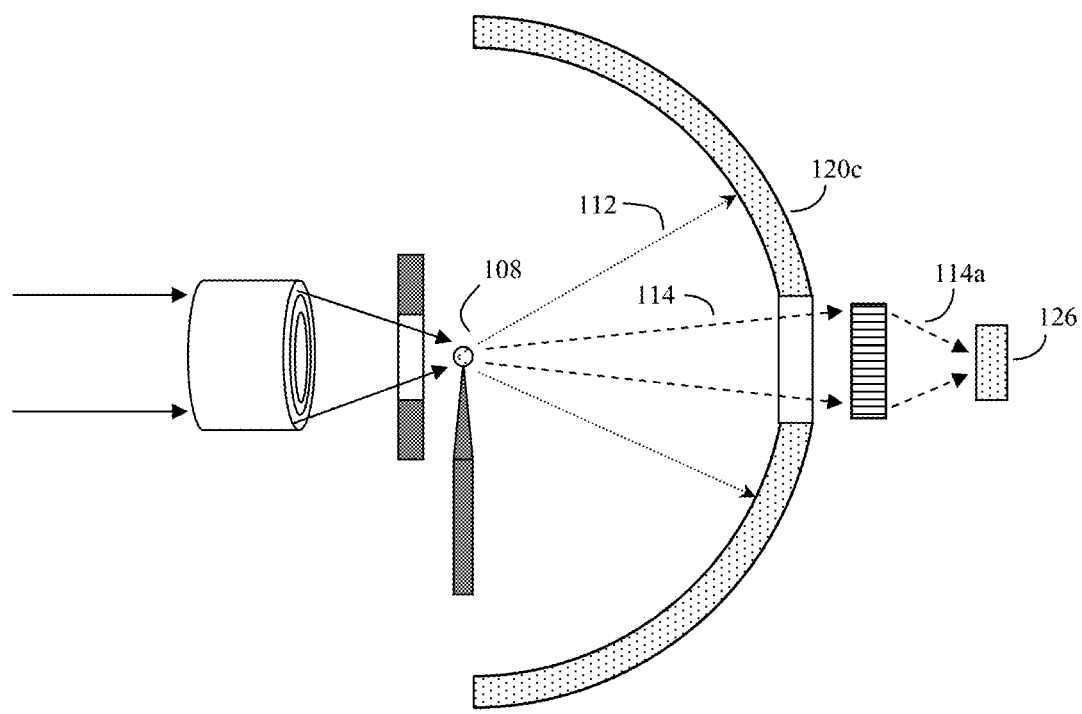
FIG. 2E shows how in some embodiments, the first outer portion of the detection apparatus may be disposed on the inner wall of a concave surface. This concave surface may be a curved surface (which may be composed of polygons) such as a portion of a smooth or polygonal sphere, or a cube or higher polygonal count concave surface.

Although in FIG. 2B, the first outer portion of the X-ray detection apparatus (120) is substantially flat and planar, other configurations are possible. In an alternative embodiment, which will be discussed in FIG. 2E shortly, various types of alternative non-planar detection apparatus, such as the inner wall of a concave surface, may be used to obtain still more X-ray diffraction information.

FIG. 2C shows a drawing of the second X-ray optical device (e.g. phase zone plate) (124) as seen from an orthogonal angle (124a), as previously discussed. In some embodiments, this phase zone plate can be produced by high resolution nanofabrication methods. Here an example fabrication pattern showing various concentric patterns of etched rings is shown. Although in a preferred embodiment, the first X-ray optical device (102) is an X-ray mirror device, the inventors do not intend to exclude the possibility that the first X-ray optical device may also be one or more phase zone plates also produced by high resolution nanofabrication methods.

Note that as shown in FIG. 2C, the central portion (125) of the phase zone plate (124a) may be left solid (e.g. contain no rings, be left unetched) so as to protect the second inner portion of the detection apparatus (126) from the damaging effects of the undeflected X-rays (116).

Put alternatively, as previously discussed, the second X-ray optical device (124) as seen from this different angle (124a), is, in a preferred embodiment, at least one phase zone plate comprising a plurality of nanometer scale phase shifting zone structures configured to focus or collimate X-rays. In other embodiments, the first X-ray optical device (102) may be a similar type device.

FIG. 2D shows a drawing of the second inner portion of the X-ray detection apparatus (126) as seen from an orthogonal angle (126a). In this example, the second X-ray optical device has used some of the narrow angle X-rays (114) that have been focused (114a) by the second X-ray optical device (124), thus forming a magnified image (134a) of the microscopy sample (108).

As previously discussed, the various X-ray optical devices receive much energy from the X-ray beams, and thus are at risk for overheating. Thus in some embodiments, the at least one phase zone plate (124, 124a) may be further configured with at least one hollow channel where a cryogenic fluid, such as liquid helium, may circulate. This is shown in more detail in FIG. 3C.

Returning to the first outer portion of the X-ray detection apparatus previously discussed in the context of FIG. 2B, one drawback of using a substantially flat or planar detection apparatus (120) is that the actual pattern of diffracted X-rays emitted by the sample (108) will tend to be spherically distributed. That is, the various diffracted X-rays (112) will tend to be spherically distributed around sample (108). Thus when a planar detection apparatus is used, one drawback is that not all diffracted X-rays (112) will be captured. Another drawback is that the various diffracted X-rays will have to travel different distances before they reach detector (120), and those diffracted X-rays that have to travel further will have a larger diameter and lower intensity, relative to those diffracted X-rays that have to travel a lesser distance.

Thus for improved performance, in some embodiments of the invention, the first outer portion of the detection apparatus can comprise the inner surface of a concave shape, such as a curved first outer portion detection surface. This concave surface can often be a portion of the interior of a sphere, such as the curved first outer portion detection surface shown in FIG. 2E as (120c), portion of the interior of a cube, or higher order polygonal concave surface, preferably approximating the inner surface of a portion of a sphere.

FIG. 2E shows how in some embodiments, the first outer portion of the detection apparatus (120c) may be disposed on the inner wall of a concave surface, such as a curve (with a smooth or facetted surface), preferably approximating the surface of a portion of a sphere. In some embodiments, this concave surface may be a polygonal curved surface composed of a plurality of many small flat detector devices, such as flat detector IC chips, where each IC chip is a facet in the polygonal sphere portion.

Thus in some embodiments, this concave first outer portion detection surface (120c) may be configured so that the spatially separated X-rays (112) that have been diffracted at various angles from the microscopy sample (108) maintain a substantially equal distance from the detection surface (120c) to the microscopy sample (108) over at least some of the various angles that the various spatially separated X-rays that have been diffracted over (with respect to the various angles from the microscopy sample 108).

As previously discussed, since often it is convenient to form X-ray detectors from various integrated circuit chips, which are usually flat semiconductor wafers. Thus the concave first outer portion detection surface need not be perfectly curved or uniform. Instead, the concave surface may be arranged more like a portion of a "disco ball", where the concave surface is formed from various facets. These facets may be relatively flat X-ray detectors, or more commonly integrated circuit chips where each integrated circuit chip has a plurality of X-ray detecting pixels. Here portions of cubes, partial polyhedra, partial truncated icosahedron, polygonal shapes, and other shapes may be used.

If a faceted surface is preferred, various options for the individual IC circuit chips may be used. Generally IC circuit chip technology favors the production of rectangular (e.g. square) integrated circuit chips. Thus in some embodiments, solid surfaces composed largely of squares may be preferred. These can include portions of cubes, portions of rhombicuboctahedrons (which generally have 18 square faces and eight triangular faces), and the like. A portion of a cube (e.g. a main square corresponding to (120), surrounded by four rectangular or square detectors (e.g. top, bottom, left, and right detectors) at right angles to the main square may be used, although due to the fact that the diffracted X-rays will be hitting the top, bottom, left, and right detectors at different angles and different distances from the sample (108) make this a less preferred embodiment.

In the rhombicuboctahedron embodiment, which approximates the surface of a sphere (or a hemisphere) more precisely, the curved first outer portion detection surface can comprise 9 square detectors, with 5 square detectors facing the beam in an unobstructed manner, with another 4 square detectors mounted slightly behind the 5 main square detectors so as to form triangular detectors (with the obstructed part masked).

In these embodiments, the concave first outer portion detection surface can comprise a plurality of flat surface detectors disposed along the curved detection surface so as to approximate the preferred portion of a sphere type curve as a plurality of smaller detection surfaces.

Figure 3A:
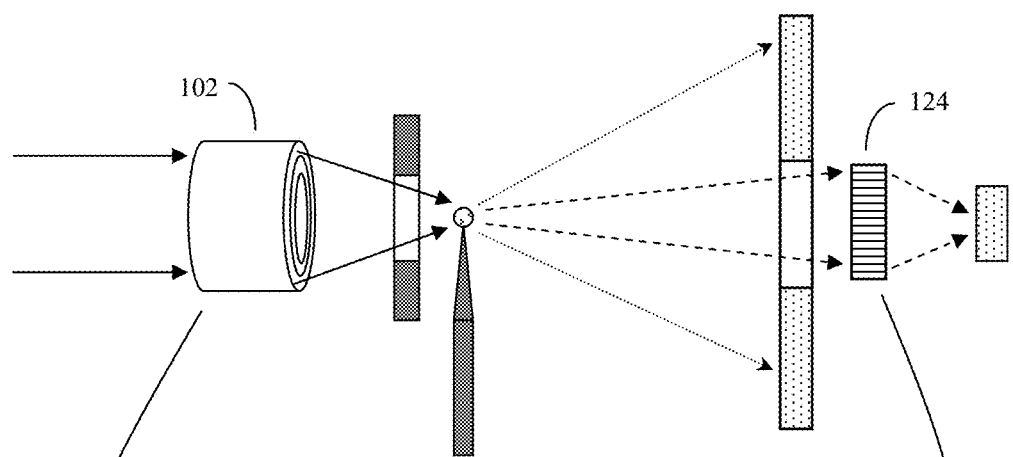
FIG. 3A again shows a detail of some of the various X-ray laser microscopy components previously shown in FIG. 1 and FIG. 2A.

FIG. 3A again shows a detail of some of the various X-ray laser microscopy components previously shown in FIG. 1 and FIG. 2A.

Figure 3B:
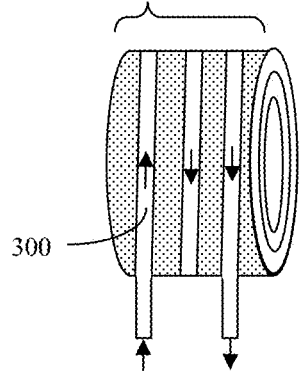
FIG. 3B shows that in some embodiments, the first X-ray optical device (e.g. the X-ray mirror device) may be cooled by running a low temperature fluid, such as liquid helium, through various hollow fixture channels.

FIG. 3B shows that in some embodiments, the first X-ray optical device (102) (e.g. the X-ray mirror device) may be cooled by running a low temperature fluid, such as liquid helium, through various hollow fixture channels (300) in the first X-ray optical device.

Figure 3C:
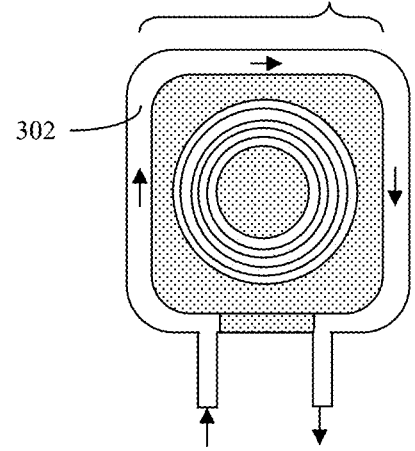
FIG. 3C shows that in some embodiments, the second X-ray optical device (e.g. the X-ray phase zone plate) may also be cooled by running a low temperature fluid, such as liquid helium, through various hollow fixture channels.

FIG. 3C shows that in some embodiments, the second X-ray optical device (124) (e.g. the X-ray phase zone plate) may also be cooled by running a low temperature fluid, such as liquid helium, through various hollow fixture channels (302) in the second X-ray optical device.

In some embodiments, it may also be useful to cool the entire interior of the vacuum chamber (400) by running either regular fluids (such as water or refrigerant fluids such as tetrafluoroethane and/or Freon family fluids) or cryogenic fluids (such as liquid nitrogen or even liquid helium) though various interior wall channels (410) in the vacuum chamber walls. This is shown in FIG. 4.

In addition to cooling the vacuum chamber itself, as well as the first X-ray optical device (102), and the second X-ray optical device (124), the performance of the system can also be improved temperature regulating various other fixtures or components as well. This is because nearly all of the components are subjected to a considerable amount of energy, either from the coherent X-rays (100) themselves, or by secondary X-rays (e.g. 112, 116), and heat produced during the X-ray microscopy process. This can result in undesired thermal expansion of the various components or fixtures, as well as other undesired effects that may degrade the performance of the system.

Thus in some embodiments, any of the various device fixtures or components, including the first X-ray optical device or X-ray mirror (102), the sample administrator (110), detection apparatus (120, 126), second X-ray optical device (124), phase zone plate (124), pinhole collimator (104) or sample chamber (to be discussed) may be further configured to be either independently temperature regulated, or else regulated as a group.

Such temperature regulation can be done by various methods, including use of thermoelectric coolers (e.g. Peltier coolers), and the like. However in a preferred embodiment, at least some of these various devices, components, or fixtures may also be configured with hollow fixture channels, as previously shown in FIGS. 3B and 3C, and cooling liquids (e.g. liquid helium, liquid nitrogen, Freon, and the like) may then be directed by suitable pumps and control mechanisms (FIG. 3D, 500a-500f) to cool these fixtures to the desired temperature to prepare the device for running, as well as during the actual X-ray analysis process itself.

Figure 3D:
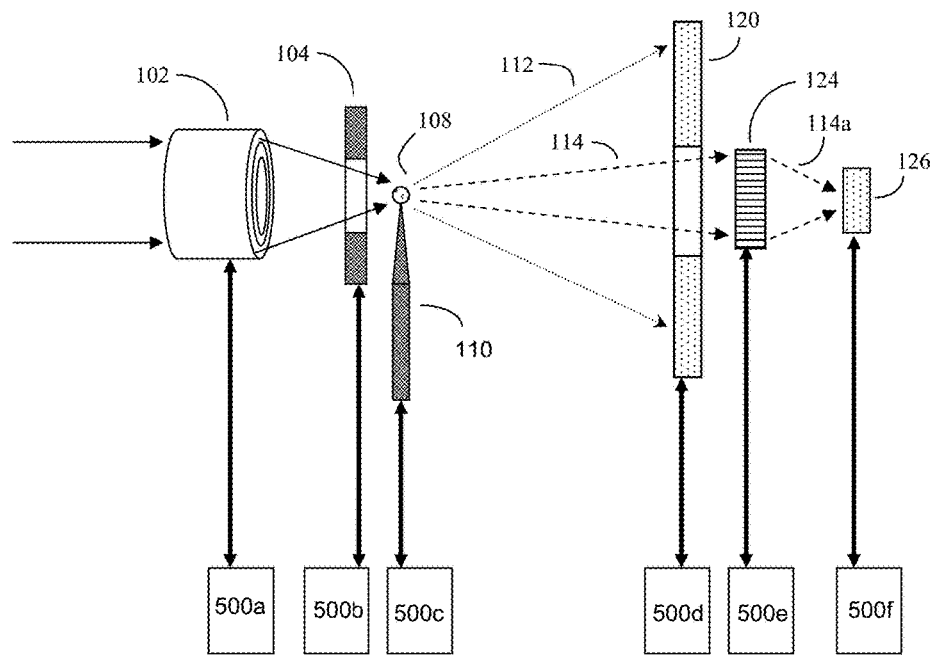
FIG. 3D shows that in some embodiments, other device components/fixtures (or device elements) may be independently temperature regulated. This can be done by using various hollow fixture channels, and running a cooling liquid through the various hollow fixture channels, as previously discussed in FIG. 3C. Note that depending on the desired temperature, different controllers and different cooling liquids or other cooling methods may be used.

FIG. 3D shows that in some embodiments, other device components/fixtures (or device elements, such as 102, 104, 110, 120, 124, 126, and others) may be independently temperature regulated. This can be done by using various hollow fixture channels, and running a cooling liquid through the various hollow fixture channels, as previously discussed in FIGS. 3B (300) and 3C (302). Note that depending on the desired temperature, different controllers, and even fixture specific controllers (500a, 500b, 500c, 500d, 500e, 500f) and different cooling liquids, or alternative cooling methods may be used.

Thus to summarize, in some embodiments, any of the devices internal fixtures, including the first X-ray optical device or X-ray mirror (102), sample administrator (110), sample chamber (see FIG. 3G), detection apparatus (e.g. 120, 126), second X-ray optical device or phase zone plate (124), and pinhole collimator (104) may be optionally configured with at least one hollow fixture channel (see FIG. 3B (300), FIG. 3C (302) as examples) and temperature controller (e.g. temperature regulated pump for a cooling liquid, 500a-500c). These various fixtures may then be independently temperature regulated (if so desired) by, for example further circulating cooling liquids through the various hollow fixture channels or tubes.

Methods of Further Improving System Resolution and Imaging Performance

In some embodiments, the second X-ray optical device can also be further optimized to improve system resolution and imaging performance. Here the problem is that although important specimen image information is obtained at low angles (114) relative to the incoming X-ray beam (100), the closer the angle gets to that of the incoming X-ray beam itself, the more that the second inner portion of the detection apparatus (126) will become oversaturated by those portions of the incoming X-ray beam (100) that have not been deflected by the sample. Indeed, prior art X-ray diffraction methods often operated by simply discarding the low angle portion of the signal (114). Here, note that "low angles" means an angle that is close to a straight angle, which only slightly deviates the angle of the incoming X-ray beam, such as within a few degrees (+/−1°, +/−2°, +/−3°) of the angle of the incoming beam.

Figure 3E:
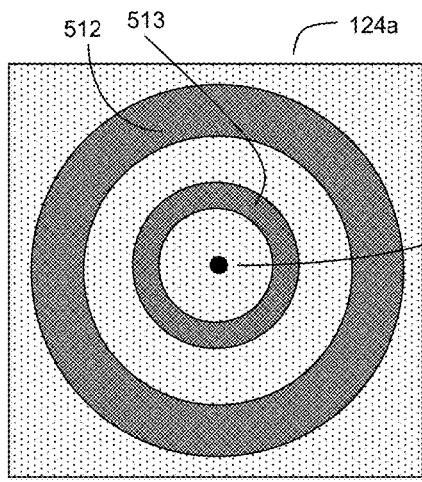
FIG. 3E shows that in some embodiments, the second X-ray optical device can comprise a central axis (e.g. be radially symmetric), and can comprise a plurality of X-ray transmissive concentric ring gaps of any of varying opening widths and varying spacing width.

In some embodiments, rather than abruptly terminating the low angle X-ray beam, the second X-ray optical device (124a, 124b) may be configured to more gradually terminate the low angle X-ray beam as the angle gets closer to zero degrees. These embodiments are shown in FIG. 3E and FIG. 3F.

In this discussion, assume that the second X-ray optical device (124) in any of FIGS. 1, 2A, 2E, 3A, 3D, 4, 5A, and 5B is replaced by either alternative second X-ray optical device (124a) or (124b).

In some embodiments, the second X-ray optical device can further comprise a central axis (510). The said second X-ray optical device can comprises a plurality of x-ray transmissive openings comprising either concentric ring gaps (FIG. 3E, 512, 513) or holes (FIG. 3F, 514, 515). These holes and concentric ring gaps can have varying spacing width, and are preferably configured so that as the holes (514, 515) or ring gaps (512, 513) move further away from the central axis (510), the opening width of the holes (514, 515) and concentric ring gaps (512, 513) increases according to a distance between the holes (514, 515) and concentric ring gaps (512, 513) and the central axis (510).

Figure 3F:
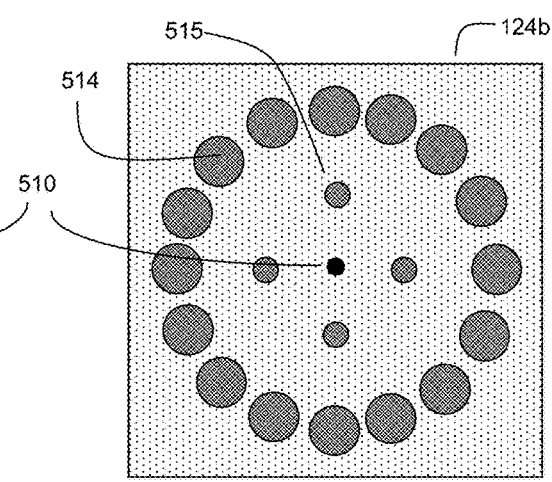
FIG. 3F shows that in some embodiments, the second X-ray optical device can comprise a central axis (e.g. be radially symmetric), and can comprise a plurality of X-ray transmissive holes with any of varying opening widths and varying spacing width (here only varying opening widths are shown).

Alternatively or additionally, the second X-ray optical device can also be configured so that the gaps (spacing width) between the various holes increase as the distance between the holes and the central axis decreases, as is shown in FIG. 3F. Indeed, in some embodiments, the ring configuration shown in FIG. 3E may also be so configured.

Thus for example, in FIG. 3F, note that the larger diameter holes (514) that are further away from the central axis (510) are also spaced closer together. By contrast, the smaller diameter holes (515) which are closer to the central axis, are spaced further apart from each other. This arrangement allows for some low angle X-ray information to pass through the second X-ray optical device (124*b*) and on to the detector (126) while still blocking most of the zero angle (not deflected by the sample) X-ray radiation from the original incoming X-ray beam (100).

Thus to summarize, FIG. 3E shows that in some embodiments, the second X-ray optical device (124, 124*a*) can comprise a central axis (510) (e.g. be radially symmetric), and can comprise a plurality of X-ray transmissive concentric ring gaps (512) of any of varying opening widths and varying spacing width.

FIG. 3F shows that in some embodiments, the second X-ray optical device (124, 124*b*) can comprise a central axis (510) (e.g. be radially symmetric), and can comprise a plurality of X-ray transmissive holes (514) with any of varying opening widths and varying spacing widths.

Maintaining the Temperature of the Sample

The sample (108) will be subjected to high amounts of energy from the X-ray illumination source (100), indeed so much that in some embodiments, the sample may be quickly destroyed during the course of the analysis. However in some embodiments, when the X-ray illumination source (100) is highly attenuated, the sample may persist for a long enough period of time that further efforts to protect the sample during the analysis may be warranted.

Figure 3G:
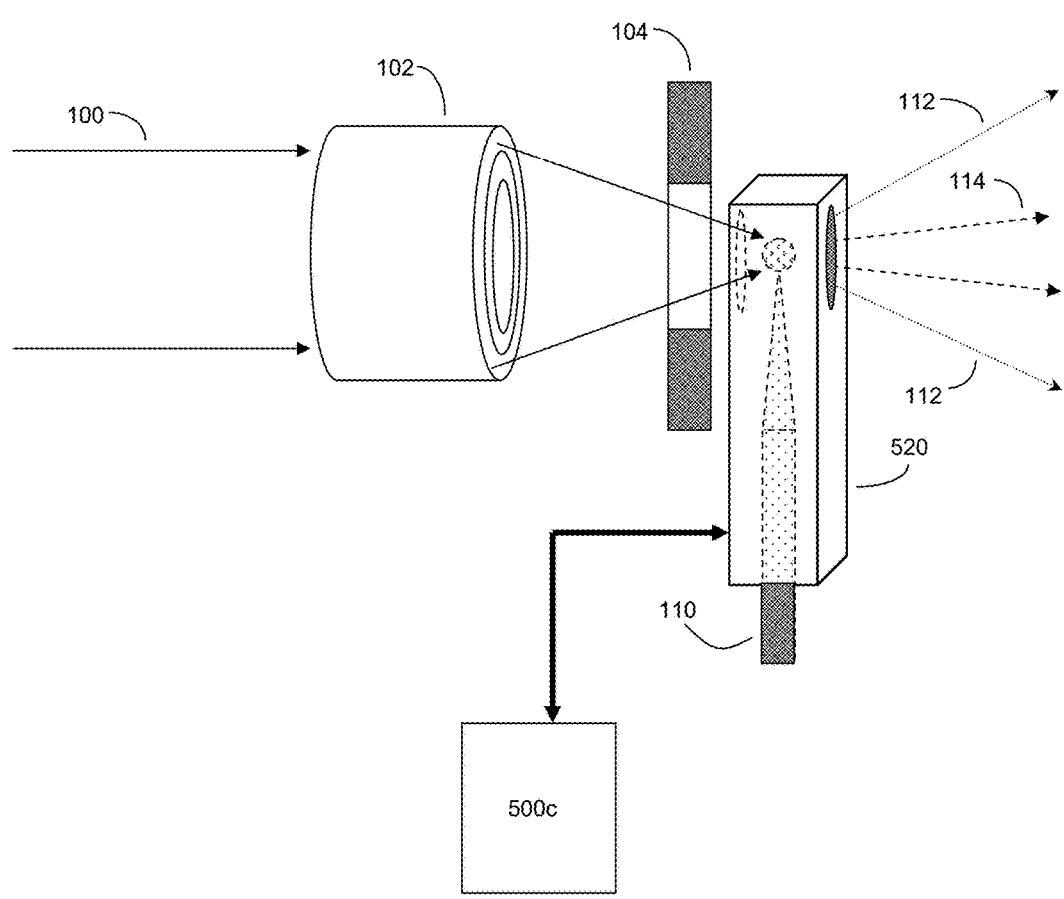
FIG. 3G shows that in some embodiments, the sample administrator may also be surrounded by its own miniature sample chamber. This miniature sample chamber can be used to help further regulate the temperature of the sample.

FIG. 3G shows that in some embodiments, the sample administrator (110) and sample (108) may also be surrounded by its own miniature sample chamber (520). This miniature sample chamber can be used to help further regulate the temperature of the sample. For example, the miniature sample chamber may have its own cooling channels, and be connected with a cooling device (500*c*). This cooling device may comprise a pump for pumping cooling liquid through channels embedded in sample chamber (520), as well as control circuitry for running this pump.

Thus in this embodiment, the sample (108), while positioned on the sample administrator (110), may be surrounded on at least four sides by a sample chamber (520), disposed in close proximity to the sample (108). This sample chamber may be further configured to further regulate the temperature and/or other environmental conditions of the sample.

Here "close proximity" means that none of the walls of the sample chamber (520) extend to enclose any of the other components except for the sample administrator (110). Specifically the optional pinhole collimator (104), the first X-ray optical device (102), the first outer portion detection apparatus (120, 120*c*), the second X-ray optical device (124, 124*a*, 124*b*), and the second inner portion detector (126, 126*a*, 126*b*) are all outside of the walls of the sample chamber. Only the sample (108) and a portion of the sample administrator (110) are inside the walls of the sample chamber (520).

FIG. 4 shows some additional components used in the improved X-ray laser microscopy method. In a preferred embodiment, components (102) to 126), previously shown in FIG. 1, may be placed inside of a vacuum chamber (400). The coherent X-rays (100) will enter into the vacuum chamber (400) through an X-ray port (402), typically comprised of an X-ray transparent material.

In a preferred embodiment, the vacuum chamber will maintain an ultra-low vacuum inside the chamber, such as a pressure of $10^{-9}$ Torr or less, and may optionally employ a sophisticated multiple stage vacuum pump system, such as the previously discussed three stage vacuum pump system (404), (406), (408), to do this.

Figure 5A:
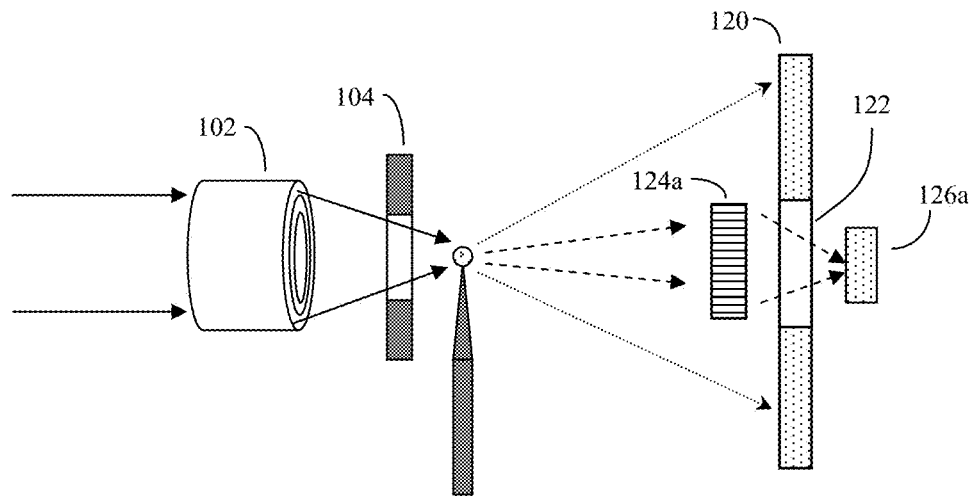
FIG. 5A shows an alternative embodiment where the second X-ray optical device (phase zone plate) and the second inner portion of the detection apparatus are disposed in a first alternative configuration

FIG. 5A shows an alternative embodiment where the second X-ray optical device (phase zone plate) (124) and the second inner portion of the detection apparatus (126) are disposed in a first alternative configuration with respect to the first outer portion of the detection apparatus (120) and optional hole (122). Here the second X-ray optical device (124*a*) is placed in front of the first outer portion of the detection apparatus (120), but the second inner portion of the detection apparatus (126*a*) is still placed behind hole (122).

Figure 5B:
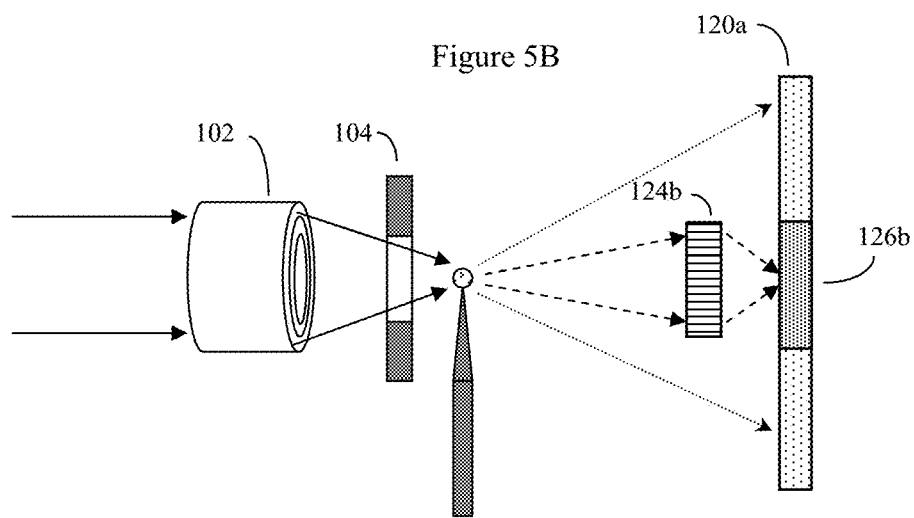
FIG. 5B shows a different alternative embodiment where the second X-ray optical device (phase zone plate) and the second inner portion of the optical detection apparatus are disposed in a second alternative configuration.

FIG. 5B shows a different alternative embodiment where the second X-ray optical device (phase zone plate) (124) and the second inner portion of the optical detection apparatus (126) are disposed in a second alternative configuration with respect to the first outer portion of the detection apparatus (120) and optional hole (122). Here the second X-ray optical device (124*b*) is placed in front of the first outer portion of the detection apparatus (120*a*), and the second inner portion of the detection apparatus (126*b*) is in the same plane as the first outer portion of the detection apparatus (120). In this embodiment, there is no hole (122).

Other Embodiments:

In some embodiments, as shown in FIGS. 1-5B, the first X-ray optical device (102) (e.g. the at least one X-ray mirror) may be entirely external to the pinhole opening in the pinhole collimator (104). However other embodiments are possible. In an alternative embodiment, however, the at least one X-ray mirror may be disposed in, or comprise, the pinhole aperture region (hole) of the pinhole collimator (104).

In some alternative embodiments, both the first X-ray optical device (102) and the second X-ray optical device (124) can be either two phase zone plates (e.g. both configured as per 124*a*) or two mirror/collimator devices (e.g. both configured as per 102/104). In other alternative embodiments, the first X-ray optical device (102) may be a phase zone plate, and the second X-ray optical device may be a mirror/collimator device (e.g. configured as per 102/104).

In some alternative embodiments, any or all surfaces that receive X-ray photons (radiation) may be coated with suitable X-ray resistant material, such as silicon, boron, silicon triboride, or other X-ray resistant material.

Software methods: In some embodiments, it may be useful to configure the at least one computer processor (132) to use various machine learning methods or neural network methods (e.g. deep neural networks, deep learning methods), to analyze both the X-ray diffraction data (128, 136) as well as X-ray imaging data (130, 134) and deduce an overall composite structure (138) of the sample (108). This overall structure will thus combine both sets of data (128, 130) to create a most likely structure (138) that is consistent with the combined data sources. Here, software libraries such as Caffe (developed by Berkeley Vision and Learning center), TensorFlow (developed by Google), and the like may be used.

The invention claimed is:

1. An X-ray laser microscopy method, said method comprising:
    obtaining an X-ray port capable of supplying a coherent source of X-ray illumination;
    obtaining a first X-ray optical device configured to focus and/or collimate X-rays;
    obtaining a sample administrator, detection apparatus, and vacuum chamber, wherein said X-ray port, first X-ray optical device, and said sample administrator are disposed inside said vacuum chamber so that said first X-ray optical device is in between said X-ray port and said sample administrator, and said sample administrator is substantially in between said first X-ray optical device and said detection apparatus;

wherein said detection apparatus comprises at least a first outer portion, said first outer portion comprising a concave first outer portion detection surface;

reducing pressure in said vacuum chamber to a pressure of $10^{-9}$ Torr or less and using said sample administrator to control a position of a microscopy sample;

chilling said first X-ray optical device to temperatures of 20 degrees Kelvin or less;

using said X-ray port to provide a burst of coherent X-rays, and using said first X-ray optical device to focus and/or collimate said burst of coherent X-rays onto said microscopy sample on said sample administrator;

using at least a first portion of said detection apparatus to detect a first signal comprising spatially separated X-rays that have been diffracted at various angles from said microscopy sample; and using at least one computer processor and said first signal to reconstruct a likely representation of a structure of said microscopy sample at a nanometer level of resolution;

wherein said vacuum chamber comprises walls configured with interior wall channels, and further cooling said vacuum chamber by circulating a fluid through said interior wall channels.

2. The method of claim 1, wherein said detection apparatus comprises at least said first outer portion and a second inner portion, further obtaining a second X-ray optical device configured to focus X rays, disposing said second X-ray optical device inside said vacuum chamber, and using said second X-ray optical device to focus X-rays obtained from said microscopy sample onto a second inner portion of said detection apparatus, thereby producing a second signal from said second X-ray optical device; and wherein said at least one computer processor is further configured to use both said first signal and said second signal to reconstruct a likely representation of a structure of said microscopy sample at a nanometer level of resolution.

3. The method of claim 2, wherein any of said first or second X-ray optical devices comprises at least one phase zone plate comprising a plurality of nanometer scale phase shifting zones structures configured to focus or collimate X-rays.

4. The method of claim 2, wherein said second X-ray optical device further comprises a central axis; and wherein said second X-ray optical device comprises a plurality of x-ray transmissive openings comprising any of holes and concentric ring gaps, said holes and concentric ring gaps being of varying spacing width.

5. The method of claim 2, wherein said second X-ray optical device further comprises a central axis; and wherein said second X-ray optical device comprises a plurality of x-ray transmissive openings comprising any of holes and concentric ring gaps;

wherein said holes and concentric ring gaps are further disposed so that an opening width of said holes and concentric ring gaps increases according to a distance between said holes and concentric ring gaps and said central axis.

6. The method of claim 2, wherein any of said first X-ray optical device, sample administrator, detection apparatus, second X-ray optical device, phase zone plate, X-ray mirror, and pinhole collimator are further configured to be independently temperature regulated.

7. The method of claim 6, wherein any of said first X-ray optical device, sample administrator, detection apparatus, second X-ray optical device, phase zone plate, X-ray mirror, and pinhole collimator is further configured with at least one hollow fixture channel, further circulating a cooling liquid through said at least one hollow fixture channel.

8. The method of claim 2, wherein said concave first outer portion detection surface is configured so that said spatially separated X-rays that have been diffracted at various angles from said microscopy sample maintain a substantially equal distance from said microscopy sample over at least some of said various angles.

9. The method of claim 8, wherein said concave first outer portion detection surface comprises a plurality of flat surface detectors disposed along said concave first outer portion detection surface so as to approximate a portion of a sphere as a plurality of smaller flat detection surfaces.

10. The method of claim 2, wherein at least said first X-ray optical device comprises at least one X-ray mirror formed from a plurality of curved X-ray reflecting surfaces, said x-ray mirror comprising any of a Wolter, Kirkpatrick-Baez, or Schwarzschild x-ray mirror design.

11. The method of claim 10, wherein said at least one X-ray mirror is configured to work in conjunction with a pinhole collimator to concentrate collimated coherent X-rays onto said microscopy sample on said sample administrator.

12. The method of claim 11, wherein said at least one X-ray mirror is entirely external to said pinhole collimator, or wherein at least one X-ray mirror of said at least one X-ray mirror is disposed in a pinhole aperture region (hole) of said pinhole collimator.

13. The method of claim 10, wherein said at least one X-ray mirror comprises any of silicon, boron, silicon triboride; or wherein any of said first or second X-ray optical devices comprises at least one phase zone plate comprising a plurality of nanometer scale phase shifting zones structures configured to focus or collimate X-rays, and said at least one phase zone plate comprises any of silicon, boron, silicon triboride.

14. The method of claim 1, wherein said sample, while positioned on said sample administrator, is surrounded on at least four sides by a sample chamber, disposed in close proximity to said sample, and configured to further regulate a temperature of said sample.

15. The method of claim 1, further using a three stage vacuum pump to reduce the pressure in said vacuum chamber to a pressure of $10^{-13}$ Torr or less.

16. The method of claim 1, wherein said burst of coherent X-rays has a time duration between $10^{-13}$ seconds (100 femtoseconds) and $10^{-17}$ seconds (10 attoseconds).

17. The method of claim 1, wherein said sample administrator comprises any of a sample holder or a sample injection port.

18. The method of claim 1, wherein said at least a first outer portion of said detection apparatus comprises a plurality of spatially separated, solid state, detector elements.

19. The method of claim 1, wherein said coherent source of X-ray illumination is provided by any of a free-electron laser, capillary plasma-discharge laser, Solid-slab target laser, optical field excited plasma laser, or high-harmonic generation laser.

* * * * *